CHRYSANTHEMUM PLANT

Filed Dec. 11, 1970 2 Sheets-Sheet 1

INVENTORS
SING LING LEE,
WALTER H. JESSEL, JR.,
WILLIAM E. DUFFETT
BY
Oberlin, Maky, Donnelly & Renner
ATTORNEYS INVENTORS
SING LING LEE,
WALTER H. JESSEL, JR.,
WILLIAM E. DUFFETT
BY
Oberlin, Maky, Donnelly & Renner
ATTORNEYS

United States Patent Office

Plant Pat. 3,249

Patented Aug. 1, 1972

3,249

CHRYSANTHEMUM PLANT

Sing Ling Lee, Mountain View, Calif., assignor to Yoder Brothers, Inc., Barberton, Ohio

Filed Dec. 11, 1970, Ser. No. 97,396

Int. Cl. A01h *5/00*

U.S. Cl. Plt.—77 1 Claim

The present invention comprises a new and distinct cultivar of chrysanthemum plant which is a sport of the cultivar known in the United States as Improved Albatross.

The new cultivar is similar in many respects to Improved Albatross, having the same characteristics of:

1. Flower color.
2. Foliage color.
3. Flowering period.

The new cultivar is distinguished from Improved Albatross by the following characteristics:

1. 5–7 days earlier and more uniform response.
2. 1″ larger and more tightly incurved flowers.
3. Less twisting and reflexing of petals, which are approximately ⅛″ wider.
4. Fewer staminodal petals.
5. Stronger, heavier stems.
6. 1″–3″ taller, depending on culture.
7. Foliage broader lobed with less serration.
8. Superior flower form and form retention.
9. Superior grade performance.

The new cultivar was selected from a flowering block of the parent variety at Mt. View, California, and was asexually reproduced by cuttings at Mt. View, California and Barberton, Ohio. The new cultivar has been found to retain its distinctive characteristics through successive propagations.

The new cultivar when grown in the vicinity of Mt. View, California, has a response period of approximately 8 weeks. The following detailed description is based on observations made of both the new and parent cultivars in Barberton, Ohio. It will be understood that the response time, blooming period, color, and total vigor of the new cultivar may vary significantly with varying environmental conditions such as temperature, day length, and light intensity. Suggested flowering of the new cultivar in the northern and western United States is from April through May and November 1 through November 15; in coastal California, April through November.

Figure 1:
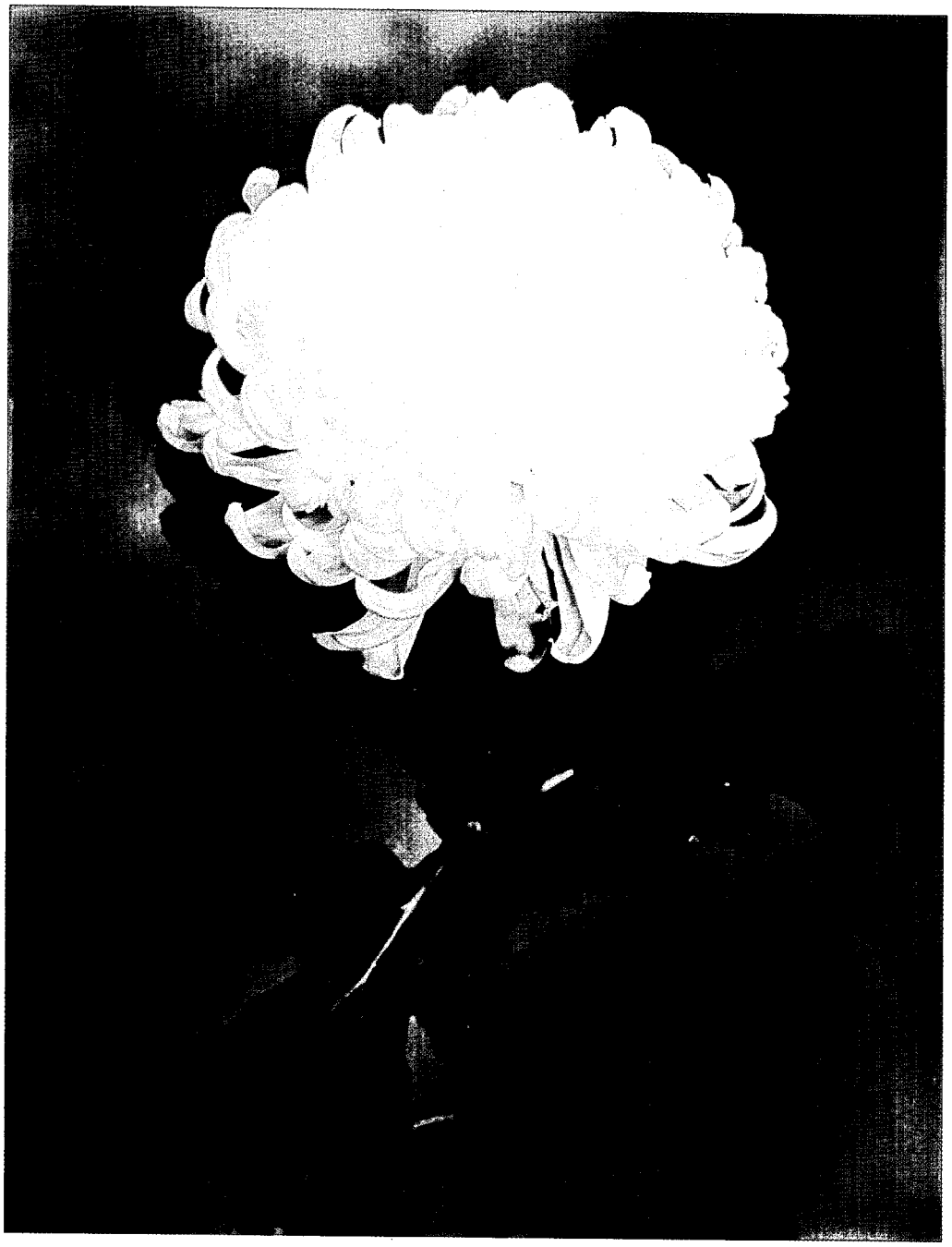
Figure 2:
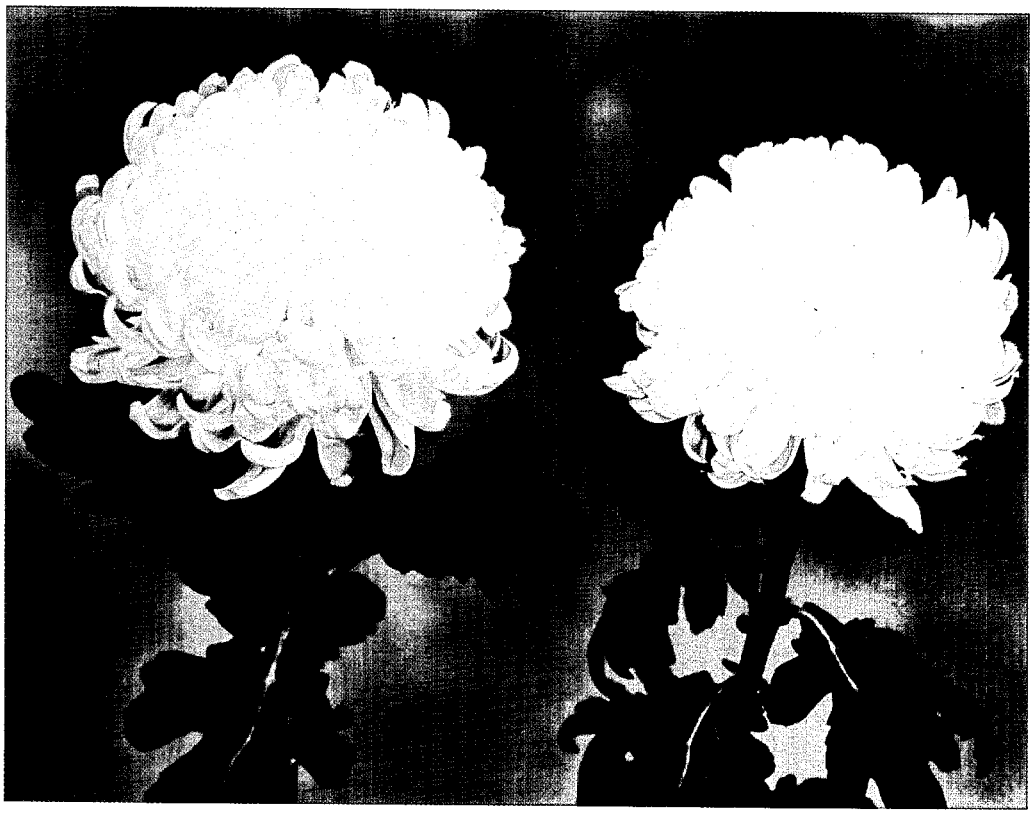

The accompanying drawings show the unique characteristics of the new cultivar, the color being as nearly true as possible with color illustrations of this type. FIG. 1 is an enlarged view of the new cultivar itself, and FIG. 2 is a comparison view with the parent cultivar Improved Albatross, with the latter appearing on the right and the new cultivar on the left.

In the description which follows, color references are to the Munsell Color Book, 1963 edition, and comparisons have been made where differences exist with the parent cultivar Improved Albatross.

Botanical Classification: *Chrysanthemum morifolium*

| | Jumbo Albatross | Improved Albatross |
|---|---|---|
| Bloom: | | |
| Fully expanded | 5½″ | 4½″. |
| Borne | 6″ | 5″. |
| Stems | Singly on disbudded plant. | Singly on disbudded plant. |
| Form | Strong | Strong. |
| Permanence | Incurve | Semi-incurve. |
| Color: | 10 days | 10 days. |
| Center of flower | Pale yellow, 7.5Y9/4 | |
| Base of petals | White, 5Y9/1 | |
| Inside of petals | do | |
| Reverse of petals | do | |
| Tonality from a distance. | White | |
| Discoloration | do | |

Petals:

*Texture.*—Smooth.

*Appearance and form.*—Open at base. Broadly keeled, tapering at terminal to an abrupt point.

*Arrangement.*—Composite, whorled on a single receptacle.

*Persistence.*—Resist shatter.

*Fragrance.*—Typical chrysanthemum.

Reproductive organs:

*Stamen, anthers.*—None to 5.

*Pollen.*—None.

*Arrangement.*—Clustered in center of flower, if present.

*Styles.*—Present both ray and disc florets.

*Length.*—Short.

*Ovaries.*—At the base of petal attached to receptacle.

Plant:

*Form.*—Herbaceous.

*Growth.*—Upright.

*Height.*—43″.

*Spread.*—None.

Foliage:

*Top side.*—Dark green, 7.5GY2/4.

*Size.*—5¾″ long, 3¼″ wide.

*Quantity.*—Numerous.

*Shape.*—Spatulate lobed.

*Texture.*—Smooth.

*Ribs and veins.*—Prominent.

*Edge.*—Moderately indented.

*Serration.*—Very slight (in Improved Albatross the serration is slight).

*Underside.*—Light green, 7.5GY4/4.

*Stipules.*—Small.

As above indicated, an important distinguishing characteristic of the new cultivar when compared with the parent cultivar Improved Albatross is its superior grade performance. This can best be seen by the following table, which shows grade data on flowering of the respective cultivars in greenhouses at Mt. View, California, under identical conditions. The grading increment is ½″, from a 6″ flower size downward. The numbers under the cultivar headings indicate the number of flowers in each size group.

| Size | Jumbo Albatross | Improved Albatross |
|---|---|---|
| 6″ | 310 | 0 |
| 5½″ | 540 | 56 |
| 5″ | 550 | 500 |
| 4½″ | 0 | 640 |
| 4″ | 0 | 300 |
| Culls | 70 | 150 |

It will thus be seen that of the total number of flowers of the new cultivar, approximately 95 percent were in the 5″–6″ size range, whereas in the flowering of the parent cultivar only approximately 33 percent of the flowers were in this 5″–6″ size range.

We claim:

1. A new and distinct cultivar of chrysanthemum which is characterized particularly as to its uniqueness when compared to the parent cultivar Improved Albatross by its 5–7 days earlier and more uniform response, 1″ larger and more tightly incurved flowers, approximately ⅛″ wider petals which undergo less twisting and reflexing, fewer staminodal petals, stronger, heavier stems, 1″–3″ taller depending on culture, foliage broader lobed with less serration, its superior flower form and form retention, and its superior grade performance.

No references cited.

ROBERT E. BAGWILL, Primary Examiner

UNITED STATES PATENT OFFICE

CERTIFICATE OF CORRECTION

Patent No. PP-3,249 Dated August 1, 1972

Inventor(s) SING LING LEE

It is certified that error appears in the above-identified patent and that said Letters Patent are hereby corrected as shown below:

Column 1, lines 61-63, should read:

| | Jumbo Albatross | Improved Albatross |
|---|---|---|
| Bloom: | | |
| Size | 5-1/2" | 4-1/2" |
| Fully expanded | 6" | 5" |

It is requested that on both sheets 1 and 2 of the drawings the following changes be made:

1) Delete "ET AL" from line 1 of the heading.

2) Delete "Walter H. Jessel, Jr." and "William E. Duffett" from the signature block.

3) In the signature block, change "INVENTORS" to --INVENTOR--.

Signed and sealed this 9th day of January 1973.

(SEAL)
Attest:

EDWARD M. FLETCHER, JR.
Attesting Officer

ROBERT GOTTSCHALK
Commissioner of Patents